(12) United States Patent
Widerström

(10) Patent No.: US 7,533,668 B1
(45) Date of Patent: May 19, 2009

(54) DISPOSABLE INHALER

(75) Inventor: Carin Widerström, Lund (SE)

(73) Assignee: AstraZeneca AB, Sodertalje (SE)

( * ) Notice: Subject to any disclaimer, the term of this patent is extended or adjusted under 35 U.S.C. 154(b) by 1826 days.

(21) Appl. No.: 09/051,443

(22) Filed: Apr. 10, 1998

Related U.S. Application Data

(63) Continuation of application No. PCT/SE98/00131, filed on Jan. 29, 1998.

(30) Foreign Application Priority Data

Feb. 7, 1997 (SE) .................................. 9700423

(51) Int. Cl.
*A61M 15/00* (2006.01)

(52) U.S. Cl. ............................. 128/203.15; 128/203.12

(58) Field of Classification Search ............ 128/203.12, 128/203.15, 203.19, 203.21, 203.23; 604/58
See application file for complete search history.

(56) References Cited

U.S. PATENT DOCUMENTS

| | | | | |
|---|---|---|---|---|
| 5,239,991 A | * | 8/1993 | Chawla et al. | 128/203.15 |
| 5,533,505 A | * | 7/1996 | Kallstrand et al. | 128/203.15 |
| 5,582,591 A | * | 12/1996 | Cheikh | 604/51 |
| 5,616,123 A | * | 4/1997 | Cheikh | 604/60 |
| 5,660,169 A | * | 8/1997 | Kallstrand et al. | 128/203.15 |
| 5,673,686 A | * | 10/1997 | Villax et al. | 128/203.15 |
| 5,743,250 A | * | 4/1998 | Gonda et al. | 128/200.14 |
| 5,797,392 A | * | 8/1998 | Keldmann et al. | 128/203.15 |
| 5,873,358 A | * | 2/1999 | Gonda et al. | 128/200.14 |
| 5,881,719 A | * | 3/1999 | Gottenauer et al. | 128/203.15 |
| 5,884,620 A | * | 3/1999 | Gonda et al. | 128/200.14 |
| 5,888,477 A | * | 3/1999 | Gonda et al. | 424/45 |
| 5,915,378 A | * | 6/1999 | Lloyd et al. | 128/200.22 |
| 5,918,594 A | * | 7/1999 | Asking et al. | 128/203.15 |
| 5,941,240 A | * | 8/1999 | Gonda et al. | 128/200.14 |
| 5,945,123 A | * | 8/1999 | Hermelin | 424/464 |
| 5,970,973 A | * | 10/1999 | Gonda et al. | 128/200.14 |
| 6,024,090 A | * | 2/2000 | Gonda et al. | 128/204.23 |
| 6,105,574 A | * | 8/2000 | Jahnsson | 128/203.15 |
| 6,214,379 B1 | * | 4/2001 | Hermelin | 424/464 |

FOREIGN PATENT DOCUMENTS

| | | | | |
|---|---|---|---|---|
| DE | 4400084 A1 | * | 6/1995 | 128/203.15 |
| DE | 44 00 084 A1 | | 7/1995 | |
| WO | WO 93/17728 | | 9/1993 | |

OTHER PUBLICATIONS

Merriam Webster's Collegiate Dictionary 10th Ed p. 1174.*
Roget's II The New Thesaurus Expanded Ed. p. 969.*
International-Type Search Report.

* cited by examiner

*Primary Examiner*—Justine R. Yu
(74) *Attorney, Agent, or Firm*—Fish & Richardson P.C.

(57) ABSTRACT

A disposable inhaler for administering medicament by inhalation having an inhalation channel through which a user may inhale, a container for containing a dose of medicament, at least one subsidiary container for containing a subsidiary dose of medicament and respective release means for selectively opening one or both of said container and said subsidiary container such that one or both of said dose and said subsidiary dose may be released into said inhalation channel at the same time so as to provide a variable dose and methods of providing a variable quantity of substance in a channel comprising opening a first container containing the substance and selectively opening a second container containing the substance.

8 Claims, 7 Drawing Sheets

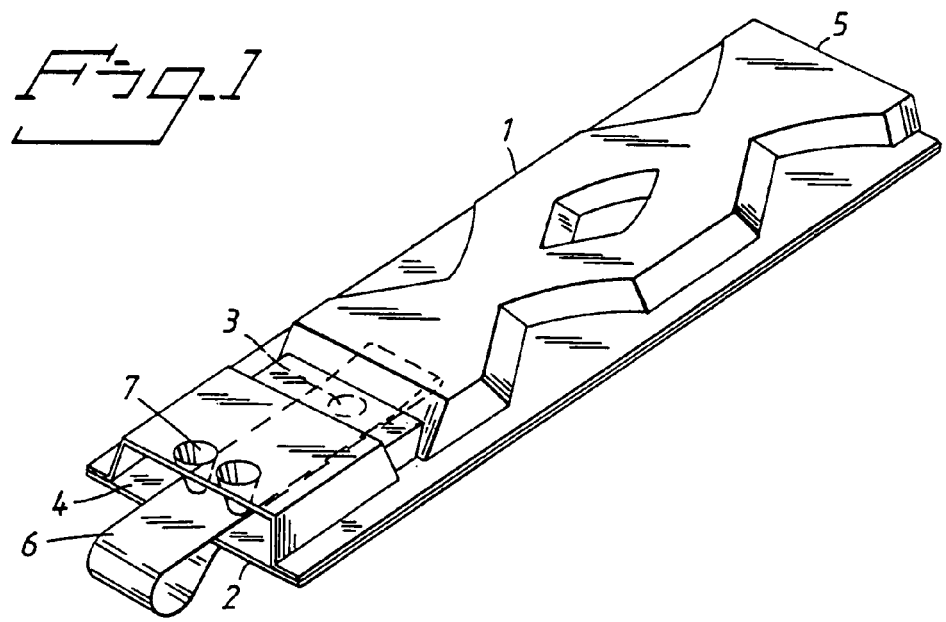
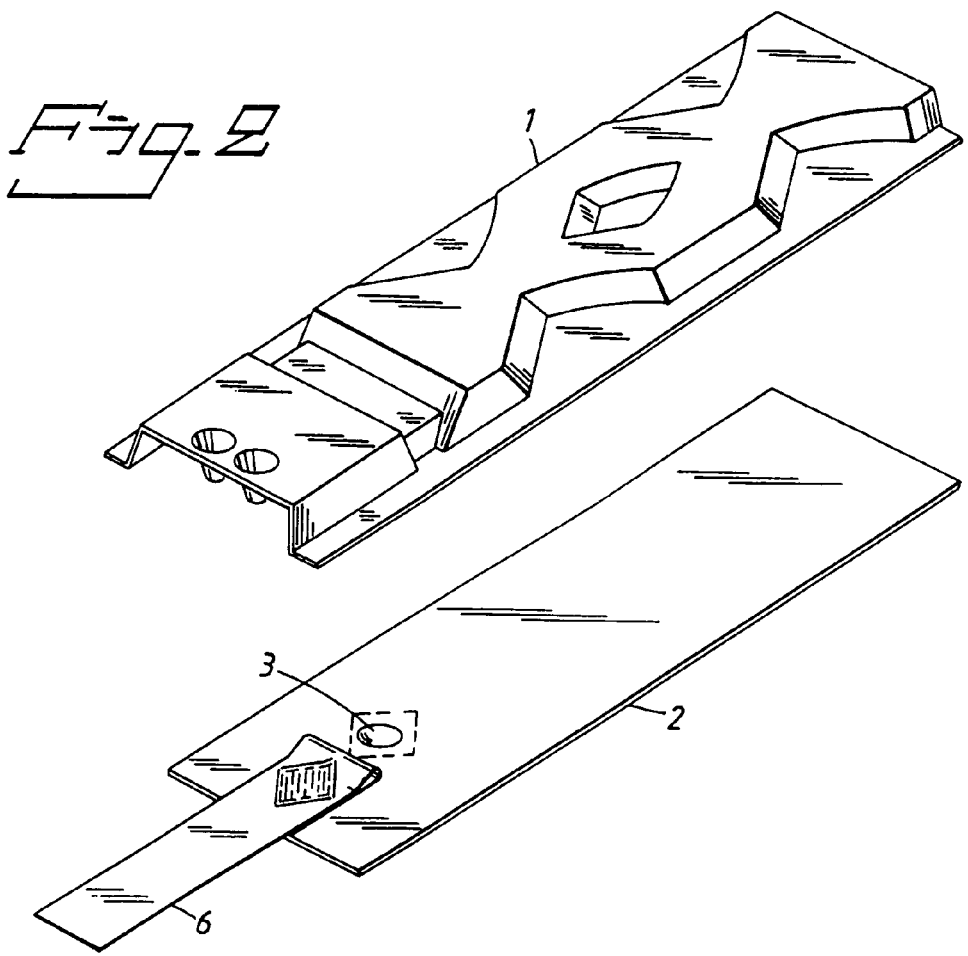

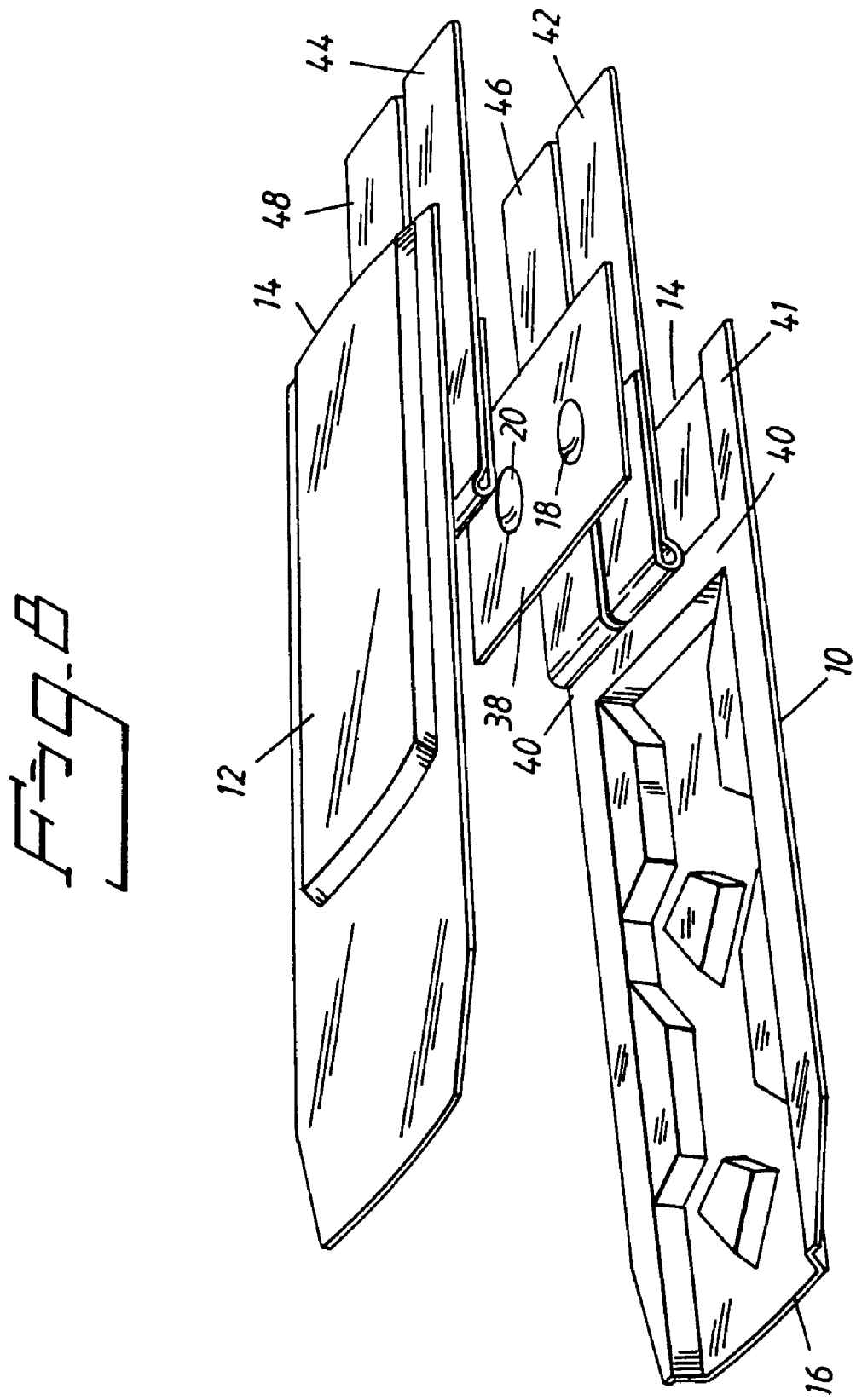

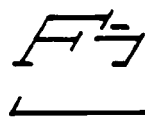
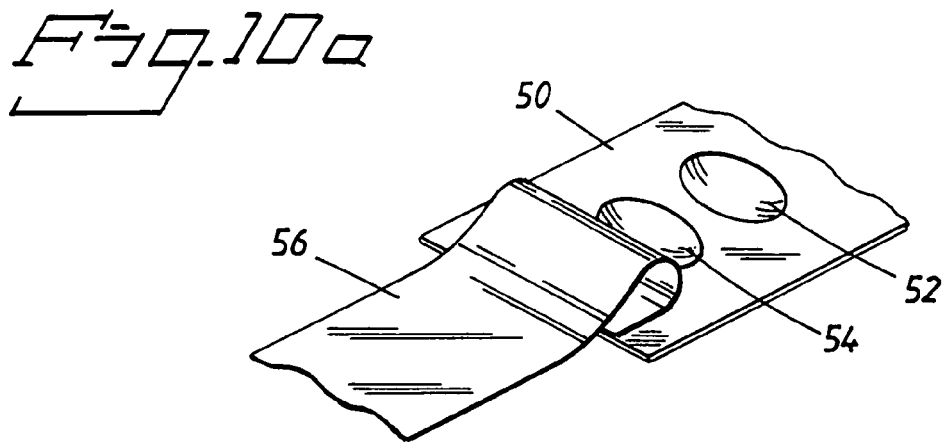
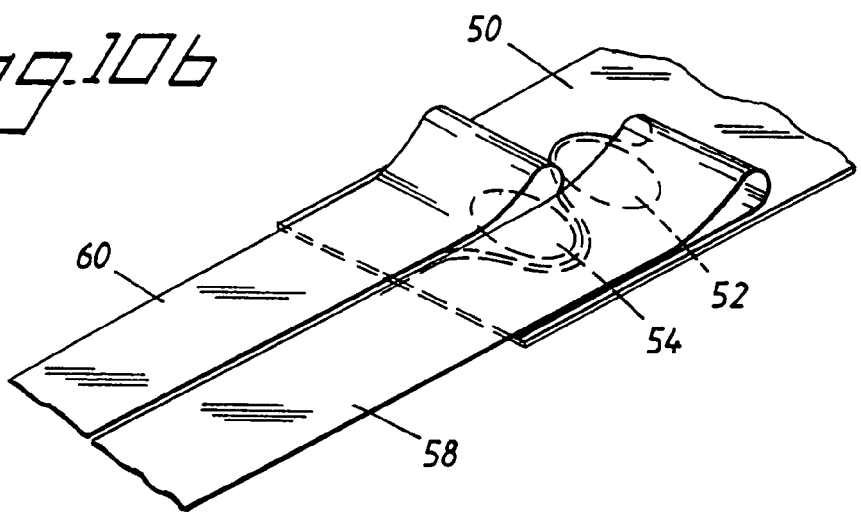
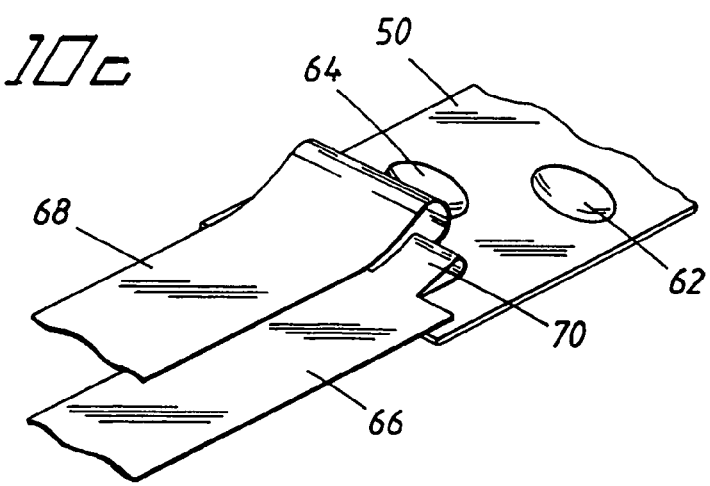

DISPOSABLE INHALER

This is a continuation of International Patent Application No. PCT/SE98/00131, with an international filing date of 29 Jan., 1998, now pending.

The present invention relates to a disposable inhaler, i.e. an inhaler intended for use only once before disposal. More particularly, it relates to a disposable inhaler which provides a variable dose and also to a method of providing a variable quantity of substance.

Previously, as described in WO93/17728 and also illustrated in FIGS. 1 and 2 of the accompanying drawings, there was known a disposable inhaler constructed from a first part 1 and a second part 2. The second part 2 includes a recess 3 in which a dose of powder is stored and the two parts together define a channel through which a stream of air may be drawn by the user. In particular, the stream of air is drawn from an air inlet 4 through to a mouthpiece 5.

As illustrated in FIG. 1, a tape 6 is provided to cover the recess 3 and extend out of the air inlet 4. The tape is additionally bent around the outside of the part 2 to cover an aperture in the bottom of the recess 3. This aperture allows a small quantity of air to enter the inhaler through the bottom of the recess 3 and assists in ensuring that all of the powder in the recess 3 joins the flow of air through the inhaler.

In use, the tape 6 is pulled from the lower surface of the second part 2 so as to expose the aperture in the bottom of the recess 3. It is then pulled out of the air inlet 4 and from the upper surface of the second part 2 to expose the recess 3, as illustrated in FIG. 2. Projections 7 are provided to prevent the loose tape 6 blocking the air inlet 4. When the user inhales through the mouthpiece 5, there is a flow of air through the inhaler and this flow picks up powder stored in the recess 3, assisted by air entering through the aperture in the bottom of the recess 3. The air/powder mixture flows through the inhaler and powder is de-agglomerated by the shape of the channel before passing out of the mouthpiece 5 and into the lungs of the user.

The inhaler described above is highly advantageous, since it provides a simple and cheap device by which powder may be de-agglomerated and inhaled without any danger of contamination of the dose or difficulty in ensuring that a complete dose is loaded into the inhaler and transferred into the air flow. Nevertheless, the present invention recognises for the first time that, in some circumstances, a user may wish to vary the dose administered. Therefore, it is an object of the present invention to provide an inhaler with which the administered dose may be varied.

According to the present invention there is provided a single use inhaler for administering medicament by inhalation, the inhaler comprising:

an inhalation channel through which a user may inhale;
a container for containing a dose of medicament; and
a release means for releasing said dose into the said inhalation channel; wherein the inhaler further comprises:

at least one subsidiary container for containing a subsidiary dose of medicament;

at least one respective subsidiary release means for releasing said subsidiary dose into said inhalation channel; wherein said release means is independently operable of said at least one subsidiary release means such that one or more of said dose and said subsidiary dose may be released into said inhalation channel at the same time and such that a variable dose is provided.

According to the present invention, there is also provided a method of providing a variable dose in a single use inhaler having an inhalation channel through which a user may inhale, a container for containing a dose of medicament and a release means for releasing said dose into said inhalation channel, said method comprising;

providing a least one subsidiary container in said single use container for containing a subsidiary dose of medicament;

providing at least one respective subsidiary release means for releasing said subsidiary dose of medicament into said inhalation channel; and arranging for said release means to be independently operable of said subsidiary release means such that one or both of said dose and said subsidiary dose may be released into said inhalation channel at the same time and such that a variable dose is provided.

According to the present invention, there is also provided a method of providing a variable quantity of substance in a channel comprising;

opening a first container containing said substance and dispensing said substance in said channel;

selectively opening a second container containing said substance according to the total quantity of substance required and dispensing said substance in said channel.

In this way, a user may selectively choose whether to release only the main dose of medicament or to release both the main and subsidiary doses of medicament. Such an inhaler may have all of the advantages known for the previous inhaler described above, but in addition, provides the user with the ability to vary the administered dose.

With the inhaler described with reference to FIGS. 1 and 2, where various different doses are required, it is necessary for a user to carry at least two inhalers containing different doses of medicament. It is also necessary for the user to be careful to replenish his supplies of inhalers according to the varying numbers of different inhalers which have been used. Furthermore, providing two or more different types of inhaler adds to the cost of manufacture and distribution.

Thus, the present invention allows a single inhaler to be manufactured, distributed and stored by a user and yet still allows the user to administer the variable dose.

This is particularly advantageous for patients having conditions such as diabetes where the dose of medicament, e.g. insulin, varies continuously according to the needs of the patient It will be appreciated that, in some circumstances, the provision of a main container and only one subsidiary container allows a user to administer three different useful doses of the same medicament. As an example, an inhaler storing four units of medicament in the main container and two units of medicament in a subsidiary container would allow the user to administer two, four or six units of that medicament.

Preferably, the inhaler is constructed similarly to the inhaler described above with said container and said at least one subsidiary container comprising depressions in a wall of said inhalation channel and said release means and said subsidiary release means respectively comprising films sealing the depressions.

Preferably, the release means and the subsidiary release means comprise one or more elongate members, such as tapes or cords, attached to said films and with respective free ends which may be pulled by a user in order to remove the films from their respective depressions.

Thus, the films may be formed, as with the inhaler described above, as an integral part of the tapes or formed from separate components. In this way, the elongate members can be used to peel the films away from the depressions.

It should be appreciated that, although a single use inhaler is referred to, it is possible that such an inhaler is used more than once. For example, where the main depression has 6 units of medicament and the subsidiary depression 2 units of medicament, if a patient requires 10 units in total, he may inhale the 6 units and 2 units from one inhaler and a further 2 units from another inhaler. Of course, this leaves the 6 units of the second inhaler unused such that, if subsequently the user requires 6 units, he could use the remaining 6 units of the second inhaler.

Medicaments suitable for use with the present invention are any which may be delivered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic- antiparasitic- and anticancer-medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N'-diacetylcystine.

As mentioned above the present invention is particularly useful with medicaments, such as insulin suitable for the treatment of conditions, such as diabetes, where the requirements of the patient vary.

The present invention will be more clearly understood from the following description, given by way of example only, with reference to the accompanying drawings in which;

FIG. 1 illustrates a previous inhaler;

FIG. 2 illustrates the previous inhaler of FIG. 1 separated into two parts;

Figure 3:
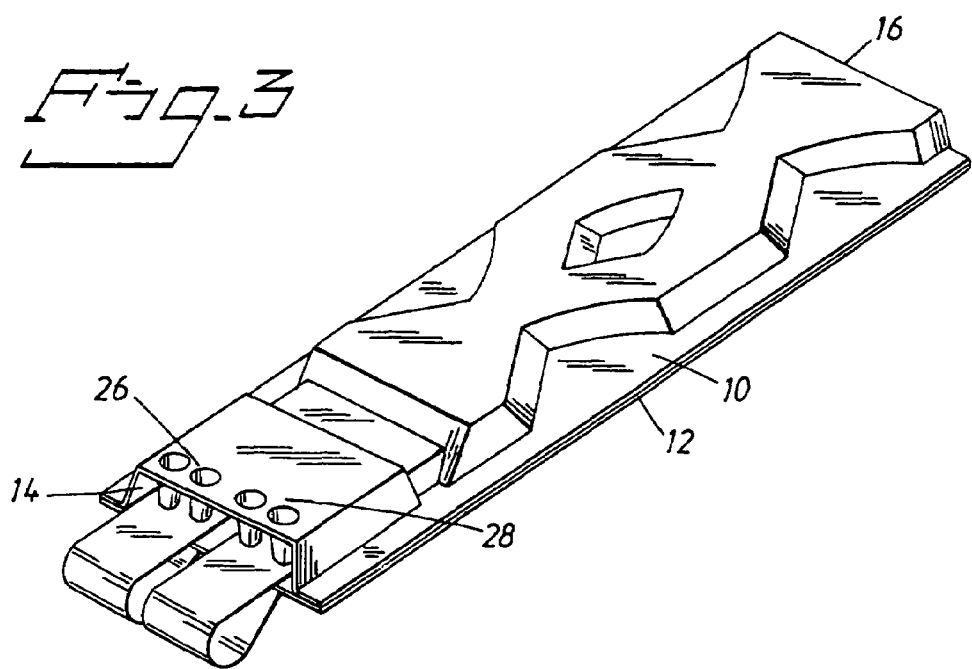
FIG. 3 illustrates an inhaler according to the present invention.
Figure 4:
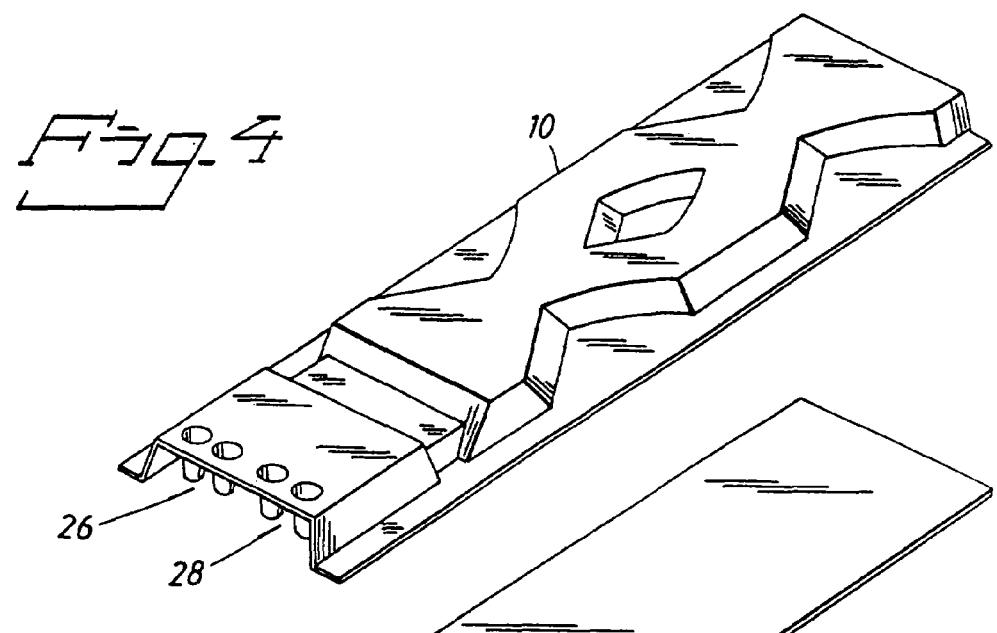
FIG. 4 illustrates the inhaler of FIG. 3 separated into two parts.
Figure 5A:
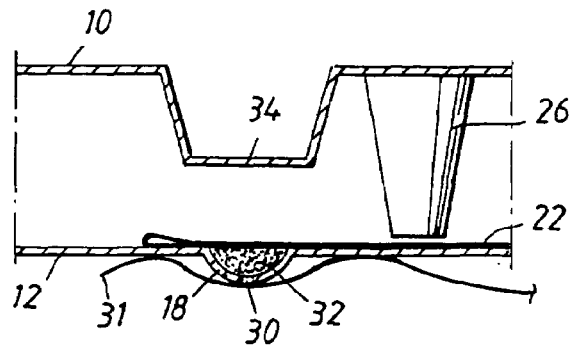
Figure 5B:
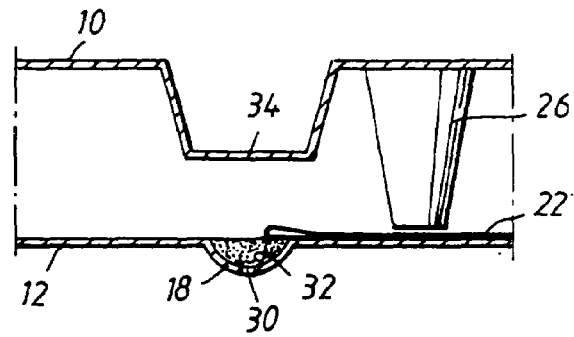
Figure 5C:
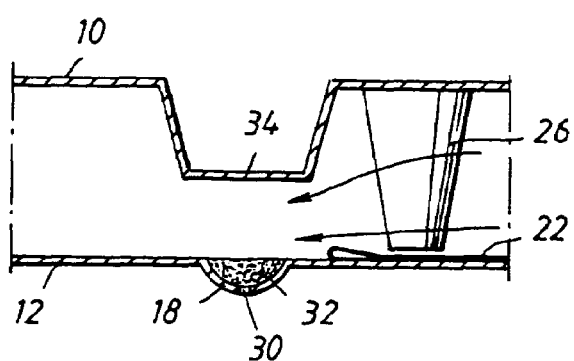
Figure 6:
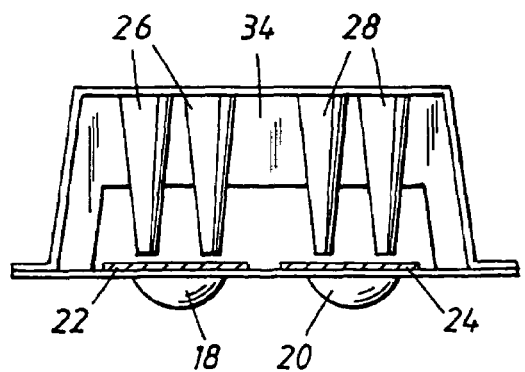
Figure 7:
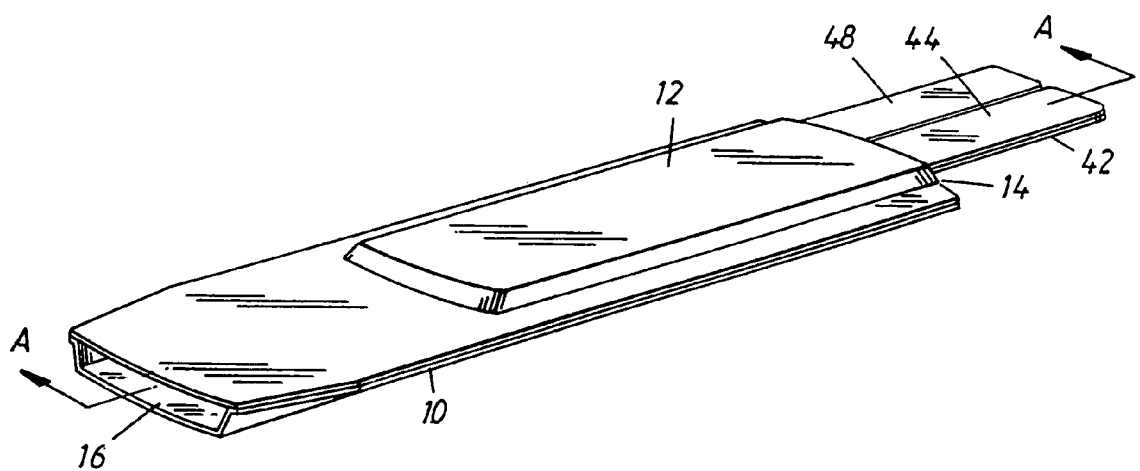
Figure 9:
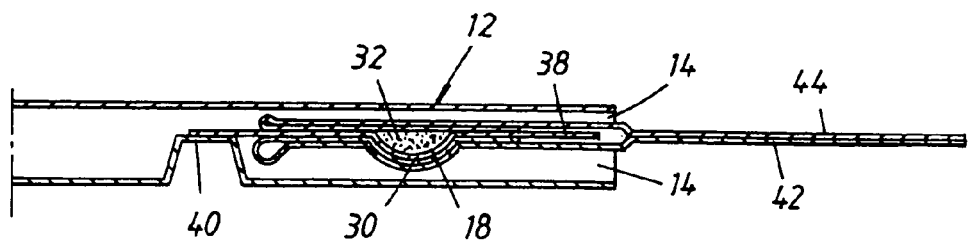

FIGS. 5(a), 5(b) and 5(c) illustrate a cross section of the inhaler of FIG. 3;

FIG. 6 illustrates a further cross section of the inhaler of FIG. 3;

FIG. 7 illustrates an inhaler according to the present invention;

FIG. 8 illustrates the inhaler of FIG. 7 separated into its component parts;

FIG. 9 illustrates a cross section of the inhaler of FIG. 7;

FIGS. 10 (a) to (e) illustrate various configurations of depressions for containing medicament.

Referring to FIGS. 3 to 6, an inhaler according to a first embodiment of the present invention will be described.

As with the inhaler described with reference to FIGS. 1 and 2, the inhaler is constructed from two parts 10 and 12 which together form an inhalation channel with an air inlet 14 and a mouthpiece 16. The inhaler differs from that described with reference to FIGS. 1 and 2 by the fact that it has two depressions 18 and 20 in place of the single depression 3. Similarly, it has two tapes 22 and 24 in place of the single tape 6 and two pairs of projections 26 and 28 in place of the single pair of projections 7.

For ease of understanding, the depression 18 and tape 22 will be described respectively as the main depression and the main tape and the depression 20 and tape 24 will be described respectively as the subsidiary depression and subsidiary tape. However, it should be appreciated that the positions of these depressions may be reversed and, furthermore, that the subsidiary depression could contain the same amount of powder as the main depression.

FIGS. 5 (a), (b) and (c) illustrate a cross section through the inhaler of FIG. 3 along a line running between the pair of projections 26. It should be appreciated that a cross section along a line running between the projections 28 would be identical.

As illustrated, the tape 22 covers the depression 18, is bent back on itself out of the air inlet 14 and back onto the lower side of the second part 12 of the inhaler so as to cover the aperture 30 formed in the bottom of the depression 18.

In use, the free end 31 of the tape 22 illustrated in FIG. 5(a) is pulled away from the lower surface of the second part 12 so as to expose the aperture 30 of the depression 18. Then, as illustrated in FIG. 5(b), the tape 22 is pulled out of the air inlet 14 so as to peel it away from the depression 18. As illustrated in FIG. 5(c), with the tape 22 pulled fully clear of the depression 18, the powder 32 contained in the depression 18 is fully exposed to the channel formed between the first part 10 and the second part 12. A restriction 34 is provided in the first part 10 so as to direct the air flow through the inhaler and, as illustrated in FIG. 5(c), down towards the depression 18. This assists in ensuring that all of the powder 32 in the depression 18 joins the air flow through the inhaler. Similarly, the aperture 30 allows some air to enter the inhaler through the bottom of the depression 18 thereby also assisting in ensuring that all of the powder 32 in the depression 18 joins the air flow through the inhaler.

Clearly, the above description applies equally to the tape 24 and the depression 20.

Thus, once a user has decided what quantity of powder should be administered, one or both of the tapes 22 and 24 are pulled away from the second surface of the lower part 12 and out of the air inlet 14. In this way, one or both of the doses of powder contained in the depressions 18 and 20 may be released into the air flow through the inhaler and inhaled into the lungs of the patient.

As with the inhaler described with reference to FIGS. 1 and 2, the first part 10 and second part 12 form a channel 36 in which de-agglomeration of powder occurs.

An inhaler according to second embodiment of the invention will be described with reference to FIGS. 7 to 10. Like parts will be given like reference numerals to those of the previous embodiment.

The first principle difference between the present embodiment and the previous embodiment concerns the position of the two depressions 18 and 20. As illustrated in FIGS. 8 and 9, the depressions 18 and 20 are provided in a separate substantially flat plate 38. The plate 38 is formed as an insert which is placed, during manufacture of the device, between the first part 10 and the second part 12 in the air flow path close to the air inlet 14 of the inhaler.

As illustrated, the first part 10 is provided with a support surface 40 for the plate 38 and the plate 38 is mounted on the support surface 40 extending towards the air inlet 14. Furthermore, the plate 38 preferably seals with sides 41 of the first part 10 so as to form a cavity with the first part 10. As illustrated in FIG. 9, the air inlet 14 allows air to enter both above the plate 38 and below it into the cavity. With the tapes 42 and 44 pulled back to expose the powder 32 in the depression 18, air entering through the air inlet 14 over the depression 18 creates a pressure difference between the region above and the region below the depression 18, thereby facilitating the release, e.g. lifting, of the dose out of the depression 18. In particular, air in the region below the depression 18 will pass through the aperture 30 in the depression 18 and assist in the release of the dose of powder 32.

The plate 38 is preferably made of aluminium or a laminate of aluminium and plastic sheet and the depression 18 is formed conveniently in the plate by using a cold-forming procedure before the plate 38 is placed in the housing. After the depression 18 has been formed in the plate 38, the powdered substance to be inhaled is filled into the depression 38 and the depression 18 sealed by means of tapes 42 and 44.

Where, as illustrated in FIG. 8, two depressions 18 and 20 are formed side by side, it is possible to form and/or fill the depressions 18 and 20 separately on separate plates. In certain systems it may advantageous to form and/or fill the depressions 18 and 20 separately when they are to contain respectively different quantities of medicament. The two plates could be joined in some manner or, in certain cases, it may be sufficient to align the plates next to one another.

As will already be apparent from the description given above and the figures, the tapes 42, 44, 46 and 48 used with the present embodiment are different to those described for the previous embodiment. In particular, each of the tapes 22 and 24 are replaced by respective pairs of tapes 42, 44 and 46, 48. FIG. 9 illustrates the case for the pair of tapes 42, 44, but clearly, the arrangement for tapes 46, 48 is preferably identical.

As illustrated, tape 44 seals depression 18 and is bent back over itself and out of the air inlet 14 in the same way as tapes 22 and 24 of the previous embodiment. However, rather than being bent back to cover the aperture 30 of the depression 18, a separate tape 42 is provided. The tape 42 seals the aperture 30 of the depression 18 and is bent back over itself and out of the air inlet 14 in the same way as the tape 44. The free ends of the tapes 42 and 44 are then preferably joined together.

In use, the free ends of tapes 42 and 44 are pulled together so as to be simultaneously peeled off the depression 18 and its aperture 30.

Depending on the particular requirements at the time, one or both of depressions 18 and 20 may be exposed by pulling one or both of the pairs of tapes 42, 44 and 46, 48.

With the present embodiment, the depressions 18 and 20, which contain the doses of powder, are contained completely within the housing of the inhaler and are thereby protected. Furthermore, the depressions 18 and 20 may be made of a suitable water impermeable substance such as aluminium, whilst molding the rest of the inhaler from a plastics material. Indeed, it is desirable to make the first 10 and second 12 parts of the inhaler from a transparent plastics material such that a user may inspect the internal air channels of the inhaler before and after use. Finally, with the arrangement described above, the tapes are less likely to be disturbed so as to expose, in particular, the apertures in the depressions 18 and 20.

The two embodiments described above have been described only with reference to two side by side depressions 18 and 20. However, subject to being able to fit the depressions into the air inlet 14 of the inhaler and/or effectively lift the powder from those depressions into the air stream through the inhaler, it is possible to provide two or more depressions and in any relative configuration.

FIGS. 10(a) to (e) illustrate schematically some other examples of how depressions and tapes may be arranged. In each of these examples, the depressions are formed in a member 50 which could be arranged as a wall of the inhaler, such as with the embodiment of FIG. 3, as a separately mounted plate, such as with the embodiment of FIG. 7, or in any other manner.

As illustrated in FIG. 10(a) it is possible to arrange two depressions 52 and 54 axially one in front of the other. It is then possible to provide two respective films for sealing the depressions 52 and 54 or a single film for sealing both depressions 52 and 54.

As illustrated, a single tape 56 is provided which initially seals both depressions 52 and 54. By peeling the tape only part way back, depression 52 is exposed and, by peeling the tape the whole way back, as illustrated, both depression 52 and depression 54 are exposed. In this embodiment, it is preferable that some means should be provided to prevent the user accidentally exposing both depressions when only the dose from depression 52 is required. By way of example, this may be achieved by providing a noticeably stronger adhesive around depression 54 or providing a band of noticeably stronger adhesive which is positioned between depression 52 and depression 54 and past which the user must pull the tape 56 before the depression 54 is exposed.

It is also possible to provide two separate tapes for the depressions 52 and 54. This may be achieved by using a tape covering depression 52 which is merely folded back over the top of the tape covering depression 54. This may also be achieved by using tapes similar to those illustrated in FIG. 10(b) where the tapes are shaped such that they may pass side by side. Although, in some ways, more complicated in structure than the overlaying arrangement, these arrangements have the advantage that both tapes 58 and 60 may be peeled back from their respective depressions independently of each other and without becoming detached from the inhaler. In this way, the chances of tapes being discarded as litter are reduced and it is possible to arrange the tapes so that either depression may be exposed without necessarily exposing the other depression. It is of course possible to devise other arrangements where parts of the tapes pass past one another while other parts overlap.

FIG. 10(c) illustrates an example where the two depressions 62 and 64 are arranged diagonally. This diagonal arrangement is particularly advantageous in providing a compromise between the side by side and in-line arrangements. It has the advantage of reduced width requirements whilst more easily allowing arrangements of tapes which pass side by side. As with the example of FIGS. 10(a) and (b), a single tape may be used or two separate overlying tapes. FIG. 10(c) actually illustrates an intermediate arrangement in which the tape 66 for covering the main depression 62 overlies the tape 68 for the subsidiary depression 64, but which has a narrowed portion 70 passing to the side of tape 68 and allowing the tape 66 to remain attached to the member 50 even when the tape 68 is peeled back to expose the subsidiary depression 64.

As will be appreciated, many other arrangements of depressions and tapes may be used, with different numbers and sizes of depressions.

Figure 10D:
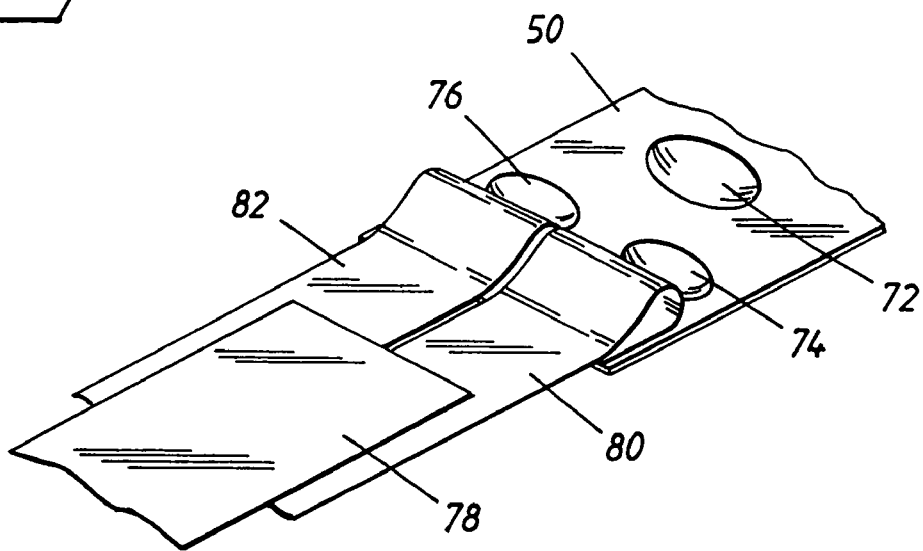

FIG. 10(d) illustrates a member 50 with a large main depression 72 and two smaller subsidiary depressions 74 and 76. A detachable tape 78 is provided for the main depression 72 and two side by side tapes 80 and 82 are provided for the subsidiary depressions 74 and 76.

Figure 10E:
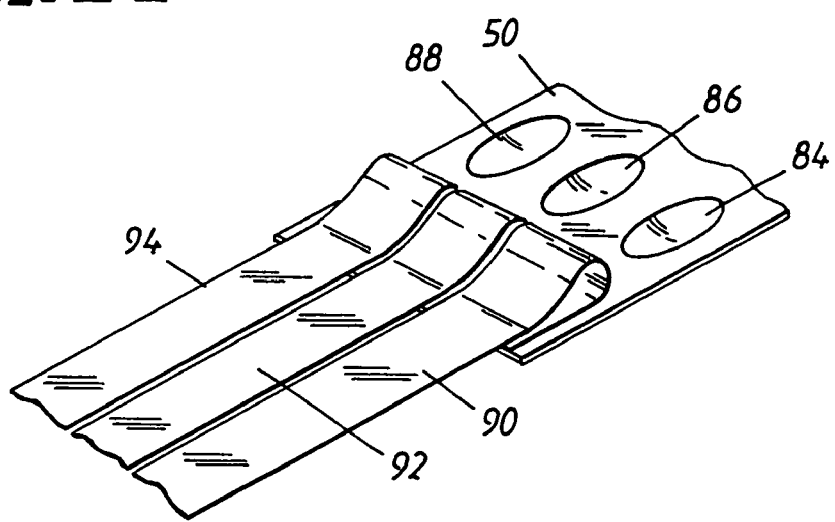

FIG. 10(e) illustrates a plate 50 with three side by side depression 84, 86 and 88 which are covered by three side by side tapes 90, 92 and 94. As illustrated, to facilitate fitting three depressions across the width of the inhaler, the depressions are not circular but elliptically elongated.

It will be appreciated that the present invention is not limited to the use of circular depressions and any suitable shaped depressions may also be used. Indeed if desired, a "depression" in the sense that this word has been used in the above description could refer to a plurality of indents, each containing part of the dose of medicament of that depression. In other words, in the embodiment of FIG. 3, the depression 18 could be replaced by a plurality of smaller indents which together contain the dose of powder contained by the equivalent single depression.

Although the description given above has been in relation to tapes which themselves seal the depressions, it will be appreciated that the important part of these embodiments are that the depressions should be sealed by a film of some sort which can be peeled away from the depressions. That film can be formed as a integral part of the tape or attached to the tape. In this way, the illustrated tapes could be replaced by films which cover the depressions and tapes or cords attached to the films for peeling the films away from the depressions. This might be particularly useful when depressions are arranged along the length of the inhaler rather than merely side by side.

Of course, it is not essential that the medicament be provided in depressions or indents and any other suitable selectively openable container may also be used.

The invention claimed is:

1. A single use inhaler for administering medicament by inhalation, the inhaler comprising:
    an inhalation channel through which a user may inhale;
    a first container containing a first dose of medicament; and
    a first release means for releasing said first dose into the said inhalation channel; wherein the inhaler further comprises:
    at least one subsidiary container containing a subsidiary dose of medicament;
    at least one respective subsidiary release means for releasing said subsidiary dose into said inhalation channel; wherein
    said first release means is independently operable of said at least one subsidiary release means such that one or more of said first dose and said subsidiary dose may be released into said inhalation channel at the same time and such that a variable dose is provided and the subsidiary dose of said at least one said subsidiary container is a predetermined fraction of said first dose that is less than said first dose.

2. An inhaler according to claim 1 wherein said first container and said at least one subsidiary container are integral parts of the inhaler.

3. An inhaler according to claim 2 wherein said first container and said at least one subsidiary container comprise depressions in at least one wall of said inhalation channel and said release means and said subsidiary release means respectively comprise films sealing said depressions.

4. An inhaler according to claim 3 wherein said first release means and said subsidiary release means comprise one or more elongate members attached to or integral with said films and with respective free ends which may be pulled by a user in order to remove the films from their respective depressions, thereby releasing the medicament contained in the respective depressions.

5. An inhaler according to claim 1, wherein said medicament is in a powdered form.

6. An inhaler according to claim 1 wherein the inhaler comprises at least two subsidiary containers containing further subsidiary doses and the further subsidiary doses of each of said at least two subsidiary containers is a predetermined fraction of said first dose that is less than said first dose.

7. An inhaler according to claim 6 wherein said subsidiary doses include different predetermined fractions of said first dose that are less than said first dose.

8. A method of providing a variable dose in a single use inhaler having an inhalation channel through which a user may inhale, a first container containing a first dose of medicament and a first release means for releasing said first dose into said inhalation channel, said method comprising;
    providing at least one subsidiary container in said single use container containing a subsidiary dose of medicament whereby the subsidiary dose of said at least one said subsidiary container is a predetermined fraction of said first dose that is less than said first dose;
    providing at least one respective subsidiary release means for releasing said subsidiary dose of medicament into said inhalation channel; and
    arranging for said first release means to be independently operable of said subsidiary release means such that one or both of said first dose and said subsidiary dose may be released into said inhalation channel at the same time and such that a variable dose is provided.

* * * * *

UNITED STATES PATENT AND TRADEMARK OFFICE
CERTIFICATE OF CORRECTION

PATENT NO. : 7,533,668 B1
APPLICATION NO. : 09/051443
DATED : May 19, 2009
INVENTOR(S) : Carin Widerström It is certified that error appears in the above-identified patent and that said Letters Patent is hereby corrected as shown below:

Column 8, line 20 (Claim 5), please delete "claim 1," and insert --claim 1-- therefor.

Signed and Sealed this

Twentieth Day of October, 2009

David J. Kappos
*Director of the United States Patent and Trademark Office*